United States Patent [19]  [11]  4,357,480
Barlow et al.  [45]  Nov. 2, 1982

[54] PROCESS FOR THE PRODUCTION OF ETHANOL BY THE LIQUID PHASE HYDROCARBONYLATION OF METHANOL

[75] Inventors: Michael T. Barlow, Addlestone; David G. Stewart, Epsom, both of England

[73] Assignee: The British Petroleum Company Limited, London, England

[21] Appl. No.: 242,488

[22] Filed: Mar. 11, 1981

[30] Foreign Application Priority Data

Mar. 18, 1980 [GB] United Kingdom ............... 8009014

[51] Int. Cl.$^3$ ............................................. C07C 29/32
[52] U.S. Cl. .................................................. 568/902
[58] Field of Search ........................................ 568/902

[56] References Cited

U.S. PATENT DOCUMENTS

| | | | |
|---|---|---|---|
| 2,549,470 | 4/1951 | Howk et al. | 568/902 |
| 3,248,432 | 4/1966 | Riley et al. | 568/902 |
| 3,387,043 | 6/1968 | Kuraishi et al. | 568/902 |
| 4,205,190 | 5/1980 | Gane et al. | 568/902 |
| 4,262,154 | 4/1981 | Gane et al. | 568/902 |
| 4,277,634 | 7/1981 | Walker | 568/902 |
| 4,283,582 | 8/1981 | Novothy | 568/902 |
| 4,328,375 | 5/1982 | Barlow | 568/902 X |

FOREIGN PATENT DOCUMENTS 1937   5/1979   European Pat. Off. ............ 568/902
2726978   1/1979   Fed. Rep. of Germany ...... 568/902

*Primary Examiner*—Bernard Helfin
*Attorney, Agent, or Firm*—Brooks, Haidt, Haffner & Delahunty

[57] ABSTRACT

A process for the production of a product comprising ethanol which process comprises reacting at elevated temperature and pressure and in the liquid phase methanol with hydrogen and carbon monoxide in the presence of an inert, particulate solid comprising a high surface area form of silica, alumina, silica/alumina or carbon, a methanol soluble catalyst comprising either:

(i) cobalt as the sole catalytic metal entity added either: as cobalt carbonyl or bis (triphenylphosphine) iminium tetracarbonylcobaltate or in a form capable of forming a carbonyl and/or carbonyl hydride complex under the prevailing reaction conditions, or (ii) a metal of Group VIII of the Periodic Table excluding iron, palladium and platinum as the sole catalytic metal entity added either as a metal complex in which the ligand is derived from cyclopentadiene or a substituted cyclopentadiene of formula: t,0010 in which R is independently hydrogen, methyl or ethyl, or in a form capable of forming the complex under the prevailing reaction conditions, and a promoter comprising either an iodide or a bromide.

10 Claims, No Drawings

PROCESS FOR THE PRODUCTION OF ETHANOL BY THE LIQUID PHASE HYDROCARBONYLATION OF METHANOL

The present invention relates to a process for the production of a product comprising ethanol by the liquid phase hydrocarbonylation of methanol.

Ethanol is a valuable industrial product which is generally manufactured either by fermentation of natural products, e.g. molasses, or by hydration of ethylene in the presence of an acid catalyst such as phosphoric acid.

The rapidly dwindling reserves of crude oil from which ethylene is derived and the associated need to utilise fully the remaining natural resources such as coal and the vast amounts of gases, e.g. methane, potentially available from the exploitation of North Sea oilfields has stimulated researches to investigate other routes to ethanol utilising these materials as feedstocks. Both coal and methane gas can be converted into synthesis gas (carbon monoxide and hydrogen), which in turn can be reacted to form methanol, which methanol can be further reacted with carbon monoxide and hydrogen in the presence of a water soluble cobalt catalyst and under appropriate conditions to form ethanol. The course of the latter reaction can be represented by the following equation.

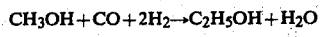

$$CH_3OH + CO + 2H_2 \rightarrow C_2H_5OH + H_2O$$

The reaction, which is generally referred to as homologation or hydrocarbonylation has been known for many years. Thus in a paper published in Science 113, 206 (1951) Wender, Friedel and Orchin reported that methanol was reacted with synthesis gas (1H$_2$:1CO) in the presence of dicobalt octacarbonyl as catalyst to produce methyl formate (2%), methyl acetate (9.0%), ethyl alcohol (38.8%), ethyl acetate (6.3%), propyl alcohol (4.7%), butyl alcohol (0.9%), methane (8.5%), propyl acetate (0.1%) and a small amount of unidentified product, the total conversion of methanol being 76.4%. Since that time many attempts to improve the yield and selectivity to ethanol have been reported. A common feature of the more recently reported work has been the addition to the cobalt catalyst of promoters such as iodides or bromides and/or organo-phosphorus compounds, e.g. phosphines. Whilst the addition of promoters has resulted in some improvement in yield and selectivity further improvements have resulted from the addition to the initial reaction mixture of various additives as described in our Belgian Pat. No. 867548 and the published specifications of our European applications Nos. 78300608.3, 79300174.4 and 78300607.5.

We have now found that surprisingly the yield and/or the selectivity to ethanol can be improved by operating the hydrocarbonylation reaction in the presence of certain inert, high surface area solids in particulate form.

Accordingly the present invention provides a process for the production of a product comprising ethanol which process comprises reacting at elevated temperature and pressure and in the liquid phase methanol with hydrogen and carbon monoxide in the presence of an inert, particulate solid comprising a high surface area form of silica, alumina, silica/alumina or carbon, a methanol soluble homologation catalyst comprising either:

(i) Cobalt as the sole catalytic metal entity added either as cobalt carbonyl or bis (triphenylphosphine) iminium tetracarbonylcobaltate or in a form capable of forming the carbonyl and/or a carbonyl/hydride complex under the prevailing reaction conditions, or (ii) a metal of Group VIII of the Periodic Table excluding iron, palladium and platinum as the sole catalytic metal entity added either as a metal complex in which the ligand is derived from cyclopentadiene or a substituted cyclopentadiene of formula:

(I)

in which R is independently hydrogen, methyl or ethyl, or in a form capable of forming the complex under the prevailing reaction conditions, and a promoter comprising either an iodide or a bromide.

The term "ligand" as used herein is defined in "Advanced Inorganic Chemistry" by F. A. Cotton and G. Wilkinson, Wiley (U.S.), 3rd edition 1972, which on page 139 defines a ligand as any atom, ion or molecule capable of functioning as the donor partner in one or more co-ordinate bonds.

The Periodic Table referred to throughout this specification is the Periodic Table of the Elements as published in the 44th Edition of the Handbook of Chemistry and Physics published by the Chemicals Rubber Publishing Company.

Methanol is a readily available industrial product. It is generally manufactured on an industrial scale from synthesis gas. Whilst it is preferred that the methanol be substantially pure the presence of small amounts of certain impurities can be tolerated. The methanol may however contain up to 50% by weight of water.

Mixtures of the gases hydrogen and carbon monoxide are abundantly available in the form of synthesis gas. Methods for preparing synthesis gas are well known in the art and usually involve the partial oxidation of a carbonaceous substance, e.g. coal. Alternatively synthesis gas may be prepared, for example, by thermal steam reforming of methane. For the purpose of the present invention the molar ratio of carbon monoxide to hydrogen may suitably be in the range 2:1 to 1:3, preferably 1:1 to 1:2. Methods for adjusting the molar ratio of carbon monoxide to hydrogen are well known to those versed in the art. Although it is preferred to use substantially pure synthesis gas the presence of such impurities as carbon dioxide and nitrogen can be tolerated. On the other hand impurities having a deleterious effect on the reaction should be avoided. Thus it may be necessary in a continuously operated process to employ a gas purge to prevent the build-up of deleterious impurities.

Cobalt as the sole catalytic metal entity in the methanol soluble catalyst may be added as cobalt carbonyl. Alternatively cobalt may be added in the form of bis(triphenylphosphine) iminium tetracarbonylcobaltate of formula [(C$_6$H$_5$)$_3$PNP(C$_6$H$_5$)$_3$]$^+$[Co(CO)$_4$]$^-$, which is available commercially. The cobalt may also be added in a form capable of forming the carbonyl and/or a carbonyl/hydride complex under the prevailing reaction conditions. The cobalt is preferably added in the ionic form, but the use of cobalt metal to react 'in situ' to form ionic cobalt which then further reacts to form the carbonyl and/or carbonyl/hydride complex is within the scope of the present invention. Typical sources of cobalt are, for example, compounds such as the carboxylate salt, e.g. the acetate, formate, propionate or the like, which under the reaction conditions form carbonyl or carbonyl/hydride complexes.

In the alternative catalyst (ii) the Group VIII metal may be added either as a metal complex in which the ligand is derived from cyclopentadiene or a substituted cyclopentadiene having the formula (I) or in a form capable of forming the complex under the prevailing reaction conditions.

Metal complexes in which the ligand is derived from cyclopentadiene or a substituted cyclopentadiene are described in 'Organometallic Compounds' by G. E. Coates, M. L. H. Green and K. Wade, Volume Two, 3rd Edition, Chapter 4, published by Methuen (1968). The π-cyclopentadienyl complexes in which the cyclopentadienyl ring is essentially covalently bonded to the metal, the metal being situated below the plane of the carbon atoms and usually equidistant from the five equivalent carbon atoms, are the preferred complexes. It is generally preferred to prepare the metal complex prior to carry out the reaction. Suitable methods for preparing the metal complex are described in the aforesaid publication entitled 'Organometallic Compounds'. One such method is by the reaction, in tetrahydrofuran, of freshly prepared sodium, potassium or thallium cyclopentadienide with an anhydrous Group VIII metal halide or other suitably soluble metal salt. Alternatively the metal complex may be prepared 'in situ' under the prevailing reaction conditions by feeding a metal salt such as the halide with sodium, potassium or thallium cyclopentadienide. Suitable Group VIII metals include cobalt, rhodium, iridium, ruthenium, nickel and osmium, of which cobalt is preferred.

With regard to the promoter the iodide or bromide can be added either in ionic form or as molecular iodine ($I_2$) or bromine ($Br_2$) or as an alkyl or aryl iodide or bromide, preferably methyl iodide. In the ionic form the iodide or bromide may be added as metal iodide or metal bromide. However, the iodide or bromide may also be added in ionic form utilising cations which are inert with regard to the hydrocarbonylation reaction. Typical of the inert form is potassium iodide or bromide, sodium iodide or bromide and lithium iodide or bromide. Of the iodide or the bromide the iodide is preferred.

The molar ratio of catalyst (i) or catalyst (ii) to the iodide or bromide may suitably be within the range from 1:5 to 10:1, preferably from 1:2 to 5:1.

The inert particulart solid suitably has a surface area greater than 100, preferably greater than 200 $m^2/g$. Silica may be present in the form of powdered glass, silica gel or a diatomaceous earth of the type known as Fullers earth, e.g. kieselguhr. Carbon may be present, for example, in the form of graphite or charcoal. Alumina may be present either alone or combined with silica in the form of a zeolite having a silica to alumina molar ratio less than 12:1, such as a large pore size Y-type zeolite. Zeolites having a higher silica to alumina molar ratio, such as the ZSM-type zeolites, tend to dehydrate methanol and for this reason their use is not preferred.

In addition to the iodide or bromide promoter there may also be added a co-promoter. Preferably the co-promoter is a compound having the general formula:

(II)

wherein X is nitrogen, phosphorous, arsenic, antimony or bismuth and A, B and C are individually monovalent hydrocarbyl groups containing from 1 to 20 carbon atoms, which hydrocarbyl groups are free from aliphatic carbon-carbon unsaturation and are bound to the X atom by a carbon/X bond, or X is phosphorus, arsenic, antimony or bismuth and any two of A, B and C together form an organic divalent cyclic ring system bonded to the X atom, or X is nitrogen and all of A, B and C together form an organic trivalent cyclic ring system bonded to the X atom.

Preferred compounds having the formula (II) are those in which X is nitrogen, phosphorus, arsenic, antimony or bismuth and A, B and C are independently monovalent hydrocarbyl groups. The hydrocarbyl groups may suitably be substituted or unsubstituted saturated aliphatic groups, saturated cycloaliphatic groups or aromatic groups, of which the unsubstituted groups are preferred.

Examples of suitable compounds having the formula (II) are triphenylamine, triphenylphosphine, triphenylarsine, triphenylstibine, triphenylbismuth, triethylphosphine, tri-n-butylphosphine, tri-t-butylphosphine, tricyclohexylphosphine, tris (4-tolyl) phosphine, tris (3-chlorophenyl) phosphine, diphenylhexylphosphine, dibutyloctadecylphosphine, tribenzylphosphine, pyridine, diphenylamine and tri-n-butylarsine. Preferred compounds having the formula (II) are triphenylphosphine, triethylphosphine and tri-n-butylphosphine.

Alternatively the co-promoter may be a polydentate ligand wherein the donor atoms are either identical or combinations of dissimilar atoms of the elements nitrogen, phosphorus, arsenic, antimony or bismuth, with the proviso that no two of the atoms are directly bonded to each other. Suitable such polydentate ligands are described in the specification accompanying our copending published European application No. 79302053. Preferably the polydentate ligand is a compound having the formula:

$$R^1R^2(X)-CR^5R^6)_n-Y(R^3)(R^4) \qquad (III)$$

wherein X and Y are independently nitrogen, phosphorus, arsenic, antimony or bismuth, n is an integer, $R^1$, $R^2$, $R^3$ and $R^4$ are idependently hydrocarbyl groups containing from 1 to 20 carbon atoms as defined in the compound of formula (II) and $R^5$ and $R^6$ are either hydrogen atoms or hydrocarbyl groups containing from 1 to 20 carbon atoms as defined for the compound of formula (II).

Illustrative of suitable compounds of formula (III) which may be used as component (iii) of the catalyst are $(C_6H_5)_2P(CH_2)$  $P(C_6H_5)_2$; $(C_6H_5)_2P(CH_2)_4P(C_6H_5)_2$ and $(C_6H_5)_2)(CH_2)_6P(C_6H_5)_2$.

The molar ratio of catalyst (i) or catalyst (ii) to the further promoter may suitably be in the range 1:1 to 1:10, preferably 1:1 to 1:3.

The term "hydrocarbyl" has been used throughout the foregoing in its accepted meaning as representing a radical formed from a hydrocarbon by removal of a hydrogen atom.

Conditions of temperature and pressure which may suitably be employed will depend to some extent on the catalyst used. Thus in the presence of catalyst (i) the elevated temperature may be in the range 150° to 250° C., preferably 180° to 230° C. In the presence of catalyst (ii) the temperature may be in the range 145° to 210° C., preferably 170° to 195° C. The elevated pressure which may be used in the presence of catalyst (i) may be greater than 50 bars, preferably in the range 50 to 300 bars, and in the presence of catalyst (ii) the pressure may be in the range 1 to 300 bars, preferably 50 to 200 bars.

The process may be carried out batchwise or continuously, continuous operation being preferred. A preferred method of operating the process continuously comprises continuously feeding synthesis gas and a liquid feed comprising methanol, catalyst (or compounds giving rise to the catalyst under the reaction conditions) and promoter or promoters to a reactor, suitably in tubular form, containing a bed of the inert, particulate solid maintained under conditions of elevated temperature and pressure and continuously removing from the reactor unreacted synthesis gas and a liquid product containing ethanol by products, unchanged methanol, catalyst and promoters. The unreacted synthesis gas may be separated and recycled to the reactor. Thereafter the liquid product may be processed, suitably by distillation, to recover light ends including ethers, by-products, ethanol, unreacted methanol, catalyst and promoter(s). The methanol, catalyst and promoter(s) may be recycled to the reactor. From the by-products there may be recovered compounds which are precursors for the formation of ethanol, e.g. 1,1-dimethoxyethane, and these may also be recycled to the reactor.

In a batch reaction it is very much preferred to maintain the inert, particulate solid in suspension by agitating the reactor contents, suitably by stirring.

Whether the solid be employed in the form of a suspension or a bed it may suitably occupy up to 50% by volume of the reactor space.

The residence time may suitably be up to 8 hours, but is preferably in the range of from 20 to 200 minutes. Short residence times are preferred because long residence times may lead to further reaction of acetaldehyde by aldol condensation-type reaction giving, for example, n-butyraldehyde. Within the context of the specification the residence time for batchwise operation is that time during which the reactor is at the specified reaction temperature. When the process is operated continuously the residence time is calculated as follows:

Residence Time (Hours) =

$$\frac{\text{Volume of the reactor occupied by the liquid phase at STP (liters)}}{\text{Total flow of liquid into the reactor (liters/hour STP)}}$$

With regard to the various ratios of reactants to be employed in the process of the invention it has already been stated that the methanol may contain up to 50% by weight of water. The molar ratio of methanol to synthesis gas fed in both continuous and batch operation may be in the range of from 10:1 to 1:20, preferably from 2:1 to 1:5. The molar ratio of catalyst (i) or catalyst (ii) to methanol may be in the range 1:10 to 1:1000, preferably from 1:4 to 1:800.

In our Belgian Pat. No. 867548 and our published European applications Nos. 78300608.3 and 79300174.4 improvements to the hydrocarbonylation of methanol with synthesis gas are disclosed, these improvements being consequent upon the deliberate addition of certain additives and solvents, such as organic acids and/or derivatives thereof, inert liquids and various oxygen-containing liquids. The inventions disclosed in these specifications are incorporated by reference into this specification.

The invention will now be illustrated by the following Examples and by reference to the following Comparison Tests in which terms such as 'the yield of realisable ethanol', 'the % Molar Yield of Realisable Ethanol', '% Molar Selectivity to Realisable Ethanol' and '% Methanol conversion' are used. These are defined as follows:

The yield of realisable ethanol is defined as the yield of free ethanol plus the yield of ethanol realisable by the hydrolysis of ethanol-yielding esters (e.g. ethyl acetate). In the same way realisable methanol is defined as the free methanol plus the methanol realisable by the hydrolysis of methanol-yielding esters (e.g. methyl acetate). Thus, % Molar Yield of Realisable Ethanol =

$$\frac{\text{Moles of realisable methanol converted into realisable ethanol} \times 100}{\text{Total moles of realisable methanol fed}}$$

and,

% Molar Selectivity of Realisable Ethanol =

$$\frac{\text{Moles of realisable methanol converted into realisable ethanol} \times 100}{\text{Total moles of realisable methanol converted}}$$

By the yield of realisable acetic acid is meant the yield of free acetic acid plus the yield of acetic acid realisable by the hydrolysis of acetic acid-yielding esters (e.g. methyl acetate). In calculating the yield it is assumed that all the acetic acid is derived from methanol and synthesis gas. Thus, % Molar Yield of Realisable Acetic Acid =

$$\frac{\text{Moles of realisable methanol converted into realisable acetic acid} \times 100}{\text{Total moles of realisable methanol fed}}$$

% Methanol conversion =

$$\frac{\text{Total moles of methanol converted}}{\text{Total moles of methanol fed}} \times 100$$

EXAMPLE 1

A stainless steel, magnetically, magnetically stirred, 300 ml autoclave equipped for high-pressure reactions was charged with cobalt acetate (6.25 g=0.025 mole), iodine (3.19 g=0.0125 mole) and triphenylphosphine (11.46 g=0.048 mole), collectively hereinafter to be referred to as Catalyst A, particulate activated alumina ($Al_2O_3$; 2.25 g) and commercial methanol (64.0 g=2.0 moles).

After purging with nitrogen, the autoclave was pressued with a 1:1 mixture of carbon monoxide and hydrogen (to about 100 bars). The reactor temperature was rapidly raised to 205° C. and the pressure adjusted to 200 bars. After two hours the autoclave was cooled to room temperature and the reaction products analysed

TABLE

| Example | Catalyst | H₂:CO molar ratio | Temp. (°C.) | Pressure (bar) | CH₃OH Conversion | EtOH (Realisable) Yield moles | EtOH (Realisable) % Molar yield | EtOH (Realisable) % Molar select | Realisable acetic acid Yield moles | Realisable acetic acid % Molar yield |
|---|---|---|---|---|---|---|---|---|---|---|
| Comp. Test 1 | A | 1:1 | 205 | 200 | 65.9 | 0.69 | 34.6 | 45.8 | 0.24 | 12.1 |
| 1 | A | 1:1 | 205 | 200 | 70.1 | 0.73 | 36.4 | 43.4 | 0.22 | 11.2 |
| 2 | A | 1:1 | 205 | 200 | 69.3 | 0.70 | 35.0 | 44.9 | 0.20 | 9.8 |
| 3 | A | 1:1 | 205 | 200 | 70.4 | 0.71 | 35.4 | 44.0 | 0.22 | 11.1 |
| Comp. Test 2 | B | 1:1 | 205 | 200 | 63.4 | 0.55 | 30.6 | 43.5 | 0.19 | 10.9 |
| 4 | B | 1:1 | 205 | 200 | 73.4 | 0.73 | 40.6 | 46.9 | 0.19 | 10.5 |
| Comp. Test 3 | C | 1:1 | 195 | 200 | 74.0 | 0.56 | 31.2 | 36.9 | 0.21 | 11.73 |
| 5 | C | 1:1 | 195 | 200 | 63.4 | 0.68 | 38.1 | 52.5 | 0.21 | 11.5 | by gas-liquid chromotography (GLC). The reaction conditions and the yield of ethanol are shown in the following Table. GLC revealed that small amounts of dimethyl ether, acetaldehyde, n-butylraldehyde, carbon dioxide and methane were formed as by-products.

COMPARISON TEST 1

Example 1 was repeated, except that particulate activated alumina (Al₂O₃) was not added to the catalyst charge.

EXAMPLE 2

Example 1 was repeated, but with the addition of 10 g of particulate activated charcoal to the catalyst charge in place of the activated alumina.

EXAMPLE 3

Example 1 was repeated, but with the addition of 5 g of particulate kieselguhr to the catalyst charge in place of the activated alumina.

EXAMPLE 4

The procedure of Example 1 was followed except that Catalyst A was replaced by acetone (8.4 g=0.245 mole), cobalt acetate (5.6 g=0.0225 mole), iodine (2.87 g=0.0113 mole) and triphenylphosphine (10.3 g=0.393 mole), hereinafter collectively referred to as Catalyst B. Furthermore only 57.8 g (1.8 moles) of methanol was added.

COMPARISON TEST 2

Example 4 was repeated except that no particulate activated alumina was added to the catalyst charge.

EXAMPLE 5

The procedure of Example 4 was followed except that Catalyst B was replaced by chlorobenzene (8.1 g=0.012 mole), cobalt acetate (5.6 g=0.0225 mole), iodine (2.87 g=0.0113 mole) and triphenylphosphine (10.3 g=0.0393 mole), hereinafter collectively referred to as Catalyst C, and the reaction temperature was 195° C. instead of 205° C.

COMPARISON TEST 3

Example 5 was repeated except that no particulate activated alumina was added to the catalyst charge.

Comparison Tests 1 to 3 are not examples in accordance with the present invention because they do not include an inert particulate solid and are included only for the purpose of comparison.

With reference to the Table Examples 1 to 3 demonstrate that the addition of an inert particulate solid increases methanol conversion and percent molar yield of realisable ethanol. In the presence of acetone the addition of particulate alumina (Example 4) increases methanol conversion, and both the percent molar yield and the percent molar selectivity to realisable ethanol. In the presence of chlorobenzene the addition of particulate alumina (Example 5) reduces the methanol conversion but increases the percent molar yield and selectivity to realisable ethanol.

We claim:

1. A process for the production of a product comprising ethanol which process comprises reacting at elevated temperature and pressure and in the liquid phase methanol with hydrogen and carbon monoxide in the presence of an inert, particulate solid comprising a high surface area form of silica, alumina, silica/alumina or carbon, a methanol soluble catalyst comprising either:
   (i) cobalt as the sole catalytic metal entity added either as cobalt carbonyl or bis(triphenylphosphine)iminium tetracarbonylcobaltate or a cobalt source capable of forming a carbonyl and/or a carbonyl hydride complex under the prevailing reaction conditions, or
   (ii) a metal complex of a metal of Group VIII of the Periodic Table excluding iron, palladium and platinum as the sole catalytic metal entity in which the ligand is derived from cyclopentadiene or a substituted cyclopentadiene of formula:

(I)

in which R is independently hydrogen, methyl or ethyl, and a promoter comprising either an iodide or a bromide.

2. A process according to claim 1 wherein the catalyst comprises cobalt as the sole catalytic metal entity as a carboxylate salt.

3. A process according to claim 1 wherein the catalyst comprises a π-cyclopentadienyl complex of cobalt.

4. A process according to claim 1, claim 2, or claim 3 wherein the promoter is iodine or an alkyl or aryl iodide.

5. A process according to claim 1, claim 2, or claim 3 wherein the molar ratio of catalyst (i) or catalyst (ii) to the iodide or bromide is in the range from 1:2 to 5:1.

6. A process according to claim 1, claim 2, or claim 3 wherein the inert particulate solid has a surface area greater than 200 m$^2$/g.

7. A process according to any one of the preceding claims wherein the inert particulate solid is present in the form of powdered glass, silica gel, a diatomaceous earth of the type known as Fullers Earth, graphite, charcoal, alumina or a zeolite having a silica to alumina molar ratio less than 12:1.

8. A process according to claim 1, claim 2, or claim 3 wherein there is also added a co-promoter which is a compound having the general formula:

(II)

wherein X is nitrogen, phosphorus, arsenic, antimony or bismuth and A, B and C are individually monovalent hydrocarbyl groups containing from 1 to 20 carbon atoms, which hydrocarbyl groups are free from aliphatic carbon-carbon unsaturation and are bound to the X atom by a carbon/X bond.

9. A process according to claim 9 wherein the co-promoter is triphenylphosphine, triethylphosphine or tri-n-butylphosphine.

10. A process according to claim 1, calim 2, or claim 3 when carried out continuously.

* * * * *

UNITED STATES PATENT AND TRADEMARK OFFICE
CERTIFICATE OF CORRECTION

PATENT NO. : 4,357,480

DATED : November 2, 1982

INVENTOR(S) : MICHAEL T. BARLOW and DAVID G. STEWART

It is certified that error appears in the above—identified patent and that said Letters Patent is hereby corrected as shown below:

Title page, in the Abstract, in the fifth line of paragraph "(ii)", after "formula:" delete "t,0010", and insert the following formula:

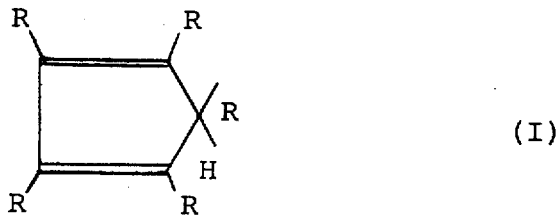

(I)

Col. 3, line 28, change "carry" to --carrying--

Col. 4, line 50, in the formula, insert a --(-- before $CR^5$.

Col. 6, line 57, delete "magnetically," first occurrence.

Col. 6, lines 65 and 66, correct the spelling of "pressured".

Col. 9, claim 7, lines 10 and 11, change "any one of the preceding claims" to read --claim 1, claim 2, or claim 3--.

UNITED STATES PATENT AND TRADEMARK OFFICE
CERTIFICATE OF CORRECTION

PATENT NO. : 4,357,480
DATED : November 2, 1982
INVENTOR(S) : MICHAEL T. BARLOW and DAVID G. STEWART It is certified that error appears in the above—identified patent and that said Letters Patent is hereby corrected as shown below:

Col. 10, claim 10, line 16, correct the spelling of "claim", second occurrence.

Signed and Sealed this

Sixth Day of March 1984

|SEAL|

Attest:

GERALD J. MOSSINGHOFF

Attesting Officer    Commissioner of Patents and Trademarks